US010379113B2

(12) United States Patent
Norvell

(10) Patent No.: US 10,379,113 B2
(45) **Date of Patent: *Aug. 13, 2019**

(54) TARGET DETECTION

(71) Applicant: DNAE Group Holdings Limited, London (GB)

(72) Inventor: Meghan E. Norvell, Albuquerque, NM (US)

(73) Assignee: DNAE Group Holdings Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/413,008

(22) Filed: Jan. 23, 2017

(65) Prior Publication Data

US 2017/0131270 A1 May 11, 2017

Related U.S. Application Data

(62) Division of application No. 14/104,164, filed on Dec. 12, 2013, now Pat. No. 9,551,704.

(60) Provisional application No. 61/739,577, filed on Dec. 19, 2012.

(51) Int. Cl.
*G01N 33/543* (2006.01)
*G01N 33/558* (2006.01)
*G01N 33/569* (2006.01)

(52) U.S. Cl.
CPC . *G01N 33/54333* (2013.01); *G01N 33/54326* (2013.01); *G01N 33/558* (2013.01); *G01N 33/569* (2013.01)

(58) Field of Classification Search
CPC ...... G01N 33/543; G01N 33/569; C12M 1/34
See application file for complete search history.

(56) References Cited

U.S. PATENT DOCUMENTS

| | | | |
|---|---|---|---|
| 3,970,518 | A | 7/1976 | Giaever |
| 4,018,886 | A | 4/1977 | Giaever |
| 4,180,563 | A | 12/1979 | Fauve |
| 4,230,685 | A | 10/1980 | Senyei et al. |
| 4,267,234 | A | 5/1981 | Rembaum |
| 4,434,237 | A | 2/1984 | Dinarello |
| 4,452,773 | A | 6/1984 | Molday |
| 4,551,435 | A | 11/1985 | Liberti et al. |
| 4,554,088 | A | 11/1985 | Whitehead et al. |
| 4,659,678 | A | 4/1987 | Forrest et al. |
| 4,677,055 | A | 6/1987 | Dodin et al. |
| 4,683,195 | A | 7/1987 | Mullis et al. |
| 4,683,202 | A | 7/1987 | Mullis |
| 4,695,393 | A | 9/1987 | Chagnon et al. |
| 4,795,698 | A | 1/1989 | Owen et al. |
| 4,851,330 | A | 7/1989 | Kohne |
| 4,901,018 | A | 2/1990 | Lew |
| 4,925,788 | A | 5/1990 | Liberti |
| 4,942,124 | A | 7/1990 | Church |
| 4,988,617 | A | 1/1991 | Landegren et al. |
| 5,004,699 | A | 4/1991 | Winters |
| 5,047,321 | A | 9/1991 | Loken et al. |
| 5,057,413 | A | 10/1991 | Terstappen et al. |
| 5,089,386 | A | 2/1992 | Stackebrandt et al. |
| 5,108,933 | A | 4/1992 | Liberti et al. |
| 5,136,095 | A | 8/1992 | Tarnowski et al. |
| 5,149,625 | A | 9/1992 | Church et al. |
| 5,164,297 | A | 11/1992 | Josephson et al. |
| 5,186,827 | A | 2/1993 | Liberti et al. |
| 5,200,084 | A | 4/1993 | Liberti et al. |
| 5,229,724 | A | 7/1993 | Zeiger |
| 5,234,816 | A | 8/1993 | Terstappen |
| 5,242,794 | A | 9/1993 | Whiteley et al. |
| 5,254,460 | A | 10/1993 | Josephson et al. |
| 5,270,163 | A | 12/1993 | Gold et al. |
| 5,338,687 | A | 8/1994 | Lee et al. |
| 5,342,790 | A | 8/1994 | Levine et al. |
| 5,460,979 | A | 10/1995 | Levine et al. |
| 5,466,574 | A | 11/1995 | Liberti et al. |
| 5,494,810 | A | 2/1996 | Barany et al. |
| 5,512,332 | A | 4/1996 | Liberti et al. |
| 5,541,072 | A | 7/1996 | Wang et al. |
| 5,583,024 | A | 12/1996 | McElroy et al. |
| 5,583,033 | A | 12/1996 | Terstappen et al. |

(Continued)

FOREIGN PATENT DOCUMENTS

| | | |
|---|---|---|
| CA | 2 342 047 A1 | 9/2001 |
| EP | 1 304 581 A2 | 4/2003 |

(Continued)

OTHER PUBLICATIONS

Grant, et al., Analysis of Multilayer Radio Frequency Microcoils for Nuclear Magnetic Resonance Spectroscopy, IEEE Trans. Magn., 37:2989-2998 (2001).
Grant, et al., NMR Spectroscopy of Single Neurons, Magn. Reson. Med., 44:19-22 (2000).
Griffiths et al., 1994, Isolation of high affinity human antibodies directly from large synthetic repertoires. EMBO J. 13(14):3245-3260.
Gu et al., 2003, Using Biofunctional Magentic Nanoparticles to Capture Vancomycin-Resistant Enterococci and Other Gram-Positive Bacteria at Ultralow Concentration, J. Am. Chem. Soc., 125:15702-15703.
Gu et al., 2006, Biofunctional magnetic nanoparticles for protein separation and pathogen detection, Chem. Commun.:941-949.

(Continued)

*Primary Examiner* — Narayan K Bhat
(74) *Attorney, Agent, or Firm* — Brown Rudnick LLP; Thomas C. Meyers

(57) ABSTRACT

The invention generally relates to methods for indicating whether an assay for isolating targets is properly isolating and detecting targets. Methods of the invention involve obtaining a sample suspected of a containing target, introducing a detectable marker into the sample, conducting an assay using magnet particles to isolate the detectable marker and the target if it is present in the sample, determining the presence or absence of the target; and confirming that the assay functioned properly by determining presence or absence of the detectable marker.

10 Claims, No Drawings

(56) References Cited

U.S. PATENT DOCUMENTS 5,597,531 A 1/1997 Liberti et al.
5,604,097 A 2/1997 Brenner
5,605,805 A 2/1997 Verwer et al.
5,622,831 A 4/1997 Liberti et al.
5,622,853 A 4/1997 Terstappen et al.
5,636,400 A 6/1997 Young
5,646,001 A 7/1997 Terstappen et al.
5,654,636 A 8/1997 Sweedler et al.
5,660,990 A 8/1997 Rao et al.
5,674,713 A 10/1997 McElroy et al.
5,677,133 A 10/1997 Oberhardt
5,681,478 A 10/1997 Lea et al.
5,684,401 A 11/1997 Peck et al.
5,695,934 A 12/1997 Brenner
5,695,946 A 12/1997 Benjamin et al.
5,698,271 A 12/1997 Liberti et al.
5,700,673 A 12/1997 McElroy et al.
5,741,714 A 4/1998 Liberti
5,768,089 A 6/1998 Finnigan
5,770,461 A 6/1998 Sakazume et al.
5,773,307 A 6/1998 Colin et al.
5,776,710 A 7/1998 Levine et al.
5,795,470 A 8/1998 Wang et al.
5,821,066 A 10/1998 Pyle et al.
5,834,217 A 11/1998 Levine et al.
5,840,580 A 11/1998 Terstappen et al.
5,846,719 A 12/1998 Brenner et al.
5,863,722 A 1/1999 Brenner
5,866,099 A 2/1999 Owen et al.
5,869,252 A 2/1999 Bouma et al.
5,876,593 A 3/1999 Liberti et al.
5,925,573 A 7/1999 Colin et al.
5,935,825 A 8/1999 Nishimura et al.
5,948,412 A 9/1999 Murphy
5,955,583 A 9/1999 Beavo et al.
5,985,153 A 11/1999 Dolan et al.
5,993,665 A 11/1999 Terstappen et al.
6,013,188 A 1/2000 Terstappen et al.
6,013,532 A 1/2000 Liberti et al.
6,060,882 A 5/2000 Doty
6,097,188 A 8/2000 Sweedler et al.
6,100,099 A 8/2000 Gordon et al.
6,120,856 A 9/2000 Liberti et al.
6,136,182 A 10/2000 Dolan et al.
6,138,077 A 10/2000 Brenner
6,146,838 A 11/2000 Williams et al.
6,150,516 A 11/2000 Brenner et al.
6,172,214 B1 1/2001 Brenner
6,172,218 B1 1/2001 Brenner
6,194,900 B1 2/2001 Freeman et al.
6,228,624 B1 5/2001 Terstappen
6,235,475 B1 5/2001 Brenner et al.
6,236,205 B1 5/2001 Ludeke et al.
6,242,915 B1 6/2001 Hurd
6,265,150 B1 7/2001 Terstappen et al.
6,287,791 B1 9/2001 Terstappen et al.
6,307,372 B1 10/2001 Sugarman et al.
6,326,787 B1 12/2001 Cowgill
6,348,318 B1 2/2002 Valkirs
6,352,828 B1 3/2002 Brenner
6,361,749 B1 3/2002 Terstappen et al.
6,361,944 B1 3/2002 Mirkin et al.
6,365,362 B1 4/2002 Terstappen et al.
6,397,094 B1 5/2002 Ludeke et al.
6,404,193 B1 6/2002 Dourdeville
6,456,072 B1 9/2002 Webb et al.
6,469,636 B1 10/2002 Baird et al.
6,487,437 B1 11/2002 Viswanathan et al.
6,495,357 B1 12/2002 Fuglsang et al.
6,512,941 B1 1/2003 Weiss et al.
6,514,415 B2 2/2003 Hatch et al.
6,551,843 B1 4/2003 Rao et al.
6,555,324 B1 4/2003 Olweus et al.
6,582,938 B1 6/2003 Su et al.
6,587,706 B1 7/2003 Viswanathan
6,594,517 B1 7/2003 Nevo
6,620,627 B1 9/2003 Liberti et al.
6,623,982 B1 9/2003 Liberti et al.
6,623,983 B1 9/2003 Terstappen et al.
6,645,731 B2 11/2003 Terstappen et al.
6,660,159 B1 12/2003 Terstappen et al.
6,696,838 B2 2/2004 Raftery et al.
6,700,379 B2 3/2004 Peck et al.
6,788,061 B1 9/2004 Sweedler et al.
6,790,366 B2 9/2004 Terstappen et al.
6,818,395 B1 11/2004 Quake et al.
6,822,454 B2 11/2004 Peck et al.
6,845,262 B2 1/2005 Albert et al.
6,858,384 B2 2/2005 Terstappen et al.
6,867,021 B2 3/2005 Maes et al.
6,876,200 B2 4/2005 Anderson et al.
6,890,426 B2 5/2005 Terstappen et al.
6,898,430 B1 5/2005 Liberti et al.
6,914,538 B2 7/2005 Baird et al.
6,958,609 B2 10/2005 Raftery et al.
7,011,794 B2 3/2006 Kagan et al.
7,056,657 B2 6/2006 Terstappen et al.
7,078,224 B1 7/2006 Bitner et al.
7,096,057 B2 8/2006 Hockett et al.
7,141,978 B2 11/2006 Peck et al.
7,169,560 B2 1/2007 Lapidus et al.
7,200,430 B2 4/2007 Thomas et al.
7,202,667 B2 4/2007 Barbic
RE39,793 E 8/2007 Brenner
7,271,592 B1 9/2007 Gerald, II et al.
7,274,191 B2 9/2007 Park et al.
7,282,180 B2 10/2007 Tibbe et al.
7,282,337 B1 10/2007 Harris
7,282,350 B2 10/2007 Rao et al.
7,304,478 B2 12/2007 Tsuda et al.
7,332,288 B2 2/2008 Terstappen et al.
7,345,479 B2 3/2008 Park et al.
7,393,665 B2 7/2008 Brenner
7,403,008 B2 7/2008 Blank et al.
7,405,567 B2 7/2008 McDowell
7,523,385 B2 4/2009 Nguyen et al.
7,537,897 B2 5/2009 Brenner et al.
7,544,473 B2 6/2009 Brenner
7,564,245 B2 7/2009 Lee
7,666,308 B2 2/2010 Scholtens et al.
7,688,777 B2 3/2010 Liberti, Jr. et al.
7,764,821 B2 7/2010 Coumans et al.
7,815,863 B2 10/2010 Kagan et al.
7,828,968 B2 11/2010 Tibbe et al.
7,863,012 B2 1/2011 Rao et al.
7,901,950 B2 3/2011 Connelly et al.
7,943,397 B2 5/2011 Tibbe et al.
8,067,938 B2 11/2011 McDowell
8,102,176 B2 1/2012 Lee
8,110,101 B2 2/2012 Tibbe et al.
8,111,669 B2 2/2012 Liberti, Jr. et al.
8,128,890 B2 3/2012 Droog et al.
8,841,104 B2 9/2014 Dryga et al.
8,889,368 B2 11/2014 Barbreau et al.
9,389,225 B2 7/2016 Dryga et al.
9,428,547 B2 8/2016 Dryga et al.
9,434,940 B2 9/2016 Dykes
9,476,812 B2 10/2016 Dryga et al.
9,551,704 B2 1/2017 Norvell
9,599,610 B2 3/2017 Sitdikov et al.
2001/0018192 A1 8/2001 Terstappen et al.
2002/0009759 A1 1/2002 Terstappen et al.
2002/0012669 A1 1/2002 Presnell et al.
2002/0098531 A1 7/2002 Thacker
2002/0130661 A1 9/2002 Raftery et al.
2002/0132228 A1 9/2002 Terstappen et al.
2002/0141913 A1 10/2002 Terstappen et al.
2002/0164629 A1 11/2002 Quake et al.
2002/0164659 A1 11/2002 Rao et al.
2002/0172987 A1 11/2002 Terstappen et al.
2003/0003441 A1 1/2003 Colston et al.
2003/0022231 A1 1/2003 Wangh et al.
2003/0054376 A1 3/2003 Mullis et al.
2003/0088181 A1 5/2003 Gleich

(56) References Cited

U.S. PATENT DOCUMENTS

2003/0092029 A1 5/2003 Josephson et al.
2003/0129676 A1 7/2003 Terstappen et al.
2003/0170613 A1* 9/2003 Straus .................... B82Y 20/00 435/5
2003/0203507 A1 10/2003 Liberti et al.
2003/0206577 A1 11/2003 Liberti et al.
2003/0222648 A1 12/2003 Fan
2004/0004043 A1 1/2004 Terstappen et al.
2004/0018611 A1 1/2004 Ward et al.
2004/0072269 A1 4/2004 Rao et al.
2004/0076990 A1 4/2004 Picard et al.
2004/0087032 A1 5/2004 Chandler et al.
2004/0101443 A1 5/2004 Kagan et al.
2004/0118757 A1 6/2004 Terstappen et al.
2004/0151629 A1 8/2004 Pease et al.
2005/0003464 A1 1/2005 Tibbe et al.
2005/0006990 A1 1/2005 Williquette et al.
2005/0026144 A1 2/2005 Maes et al.
2005/0043521 A1 2/2005 Terstappen et al.
2005/0069900 A1 3/2005 Lentrichia
2005/0079520 A1 4/2005 Wu
2005/0111414 A1 5/2005 Liberti et al.
2005/0128985 A1 6/2005 Liberti et al.
2005/0181353 A1 8/2005 Rao et al.
2005/0181463 A1 8/2005 Rao et al.
2005/0245814 A1 11/2005 Anderson et al.
2006/0024756 A1 2/2006 Tibbe et al.
2006/0115380 A1 6/2006 Kagan et al.
2006/0129237 A1 6/2006 Imran
2006/0129327 A1 6/2006 Kim et al.
2006/0147901 A1 7/2006 Jan et al.
2006/0194192 A1 8/2006 Rao et al.
2006/0233712 A1 10/2006 Penades et al.
2006/0257847 A1 11/2006 Scholtens et al.
2006/0257945 A1 11/2006 Masters et al.
2006/0281094 A1 12/2006 Squirrell et al.
2007/0037173 A1 2/2007 Allard et al.
2007/0037231 A1 2/2007 Sauer-Budge et al.
2007/0090836 A1 4/2007 Xiang et al.
2007/0114181 A1 5/2007 Li et al.
2007/0116602 A1 5/2007 Lee
2007/0117158 A1 5/2007 Coumans et al.
2007/0152669 A1 7/2007 Park et al.
2007/0152670 A1 7/2007 Park et al.
2007/0154960 A1 7/2007 Connelly et al.
2007/0166835 A1 7/2007 Bobrow et al.
2007/0183935 A1 8/2007 Clemmens et al.
2007/0231926 A1 10/2007 Ikeda
2007/0264629 A1 11/2007 Holmes et al.
2007/0296413 A1 12/2007 Park et al.
2008/0026451 A1 1/2008 Braman et al.
2008/0042650 A1 2/2008 McDowell
2008/0081330 A1 4/2008 Kahvejian
2008/0099715 A1 5/2008 Adams et al.
2008/0113350 A1 5/2008 Terstappen
2008/0135490 A1 6/2008 Li et al.
2008/0199851 A1 8/2008 Egan et al.
2008/0204011 A1 8/2008 Shoji
2008/0204022 A1 8/2008 Sillerud et al.
2008/0272788 A1 11/2008 McDowell
2008/0286838 A1 11/2008 Yuan et al.
2008/0315875 A1 12/2008 Sillerud
2009/0026082 A1 1/2009 Rothberg et al.
2009/0061456 A1 3/2009 Allard et al.
2009/0061476 A1 3/2009 Tibbe et al.
2009/0061477 A1 3/2009 Tibbe et al.
2009/0127589 A1 5/2009 Rothberg et al.
2009/0134869 A1 5/2009 Lee
2009/0136946 A1 5/2009 Connelly et al.
2009/0146658 A1 6/2009 McDowell et al.
2009/0148847 A1 6/2009 Kokoris et al.
2009/0156572 A1 6/2009 Ikeura et al.
2009/0173681 A1 7/2009 Siddiqi
2009/0191535 A1 7/2009 Connelly et al.
2009/0227044 A1 9/2009 Dosev et al.
2009/0246796 A1 10/2009 Bernard et al.
2009/0256572 A1 10/2009 McDowell
2009/0258365 A1 10/2009 Terstappen et al.
2009/0286264 A1 11/2009 Scholtens et al.
2010/0035252 A1 2/2010 Rothberg et al.
2010/0068723 A1 3/2010 Jovanovich et al.
2010/0072994 A1 3/2010 Lee et al.
2010/0129785 A1 5/2010 Pris et al.
2010/0137143 A1 6/2010 Rothberg et al.
2010/0144005 A1 6/2010 Bin Kingombe et al.
2010/0188073 A1 7/2010 Rothberg et al.
2010/0197507 A1 8/2010 Rothberg et al.
2010/0219824 A1 9/2010 Sillerud et al.
2010/0225315 A1 9/2010 McDowell
2010/0282617 A1 11/2010 Rothberg et al.
2010/0282788 A1 11/2010 Liberti
2010/0300559 A1 12/2010 Schultz et al.
2010/0300895 A1 12/2010 Nobile et al.
2010/0301398 A1 12/2010 Rothberg et al.
2010/0304982 A1 12/2010 Hinz et al.
2010/0326587 A1 12/2010 Kagan et al.
2011/0014686 A1 1/2011 Tibbe et al.
2011/0018538 A1 1/2011 Lee
2011/0044527 A1 2/2011 Tibbe et al.
2011/0046475 A1 2/2011 Assif et al.
2011/0052037 A1 3/2011 Coumans et al.
2011/0059444 A1 3/2011 Stromberg et al.
2011/0070586 A1 3/2011 Slezak et al.
2011/0086338 A1 4/2011 Hwang et al.
2011/0091987 A1 4/2011 Weissleder et al.
2011/0098623 A1 4/2011 Zhang et al.
2011/0104718 A1 5/2011 Rao et al.
2011/0137018 A1 6/2011 Chang-Yen et al.
2011/0183398 A1 7/2011 Dasaratha et al.
2011/0262893 A1 10/2011 Dryga et al.
2011/0262925 A1 10/2011 Dryga et al.
2011/0262926 A1 10/2011 Esch et al.
2011/0262927 A1 10/2011 Dryga et al.
2011/0262932 A1 10/2011 Esch et al.
2011/0262933 A1 10/2011 Dryga et al.
2011/0262989 A1 10/2011 Clarizia et al.
2011/0263833 A1 10/2011 Dryga et al.
2011/0300551 A1 12/2011 Rao et al.
2011/0300609 A1 12/2011 Lim et al.
2011/0301042 A1 12/2011 Steinmann et al.
2012/0045828 A1 2/2012 Davis et al.
2012/0094275 A1 4/2012 Rao et al.
2012/0100546 A1 4/2012 Lowery, Jr. et al.
2012/0112744 A1 5/2012 McDowell et al.
2013/0109590 A1 5/2013 Clarizia et al.
2013/0196341 A1 8/2013 Neely et al.
2013/0203634 A1 8/2013 Jovanovich et al.
2013/0316355 A1 11/2013 Dryga et al.
2014/0100136 A1 4/2014 Clarizia et al.
2014/0170021 A1 6/2014 Dryga
2014/0170639 A1 6/2014 Norvell
2014/0170640 A1 6/2014 Dykes
2014/0170641 A1 6/2014 Macemon
2014/0170652 A1 6/2014 Sitdikov et al.
2014/0170667 A1 6/2014 Dykes et al.
2014/0170669 A1 6/2014 Vandervest
2014/0170727 A1 6/2014 Dryga et al.
2014/0171340 A1 6/2014 Dykes et al.
2015/0212079 A1 7/2015 Dryga et al.

FOREIGN PATENT DOCUMENTS

EP 2138835 A1 12/2009
EP 2261650 A2 12/2010
WO 1988/003957 A1 6/1988
WO 89/06699 A1 7/1989
WO 90/08841 A1 8/1990
WO 91/02811 A1 3/1991
WO 92/08805 A1 5/1992
WO 92/15883 A1 9/1992
WO 95/31481 A1 11/1995
WO 98/20148 A1 5/1998
WO 99/53320 A1 10/1999
WO 01/73460 A1 10/2001

(56) References Cited

FOREIGN PATENT DOCUMENTS

| | | | |
|---|---|---|---|
| WO | 02/98364 | A2 | 12/2002 |
| WO | 2005/026762 | A1 | 3/2005 |
| WO | 2005106480 | A1 | 11/2005 |
| WO | 2007/018601 | A1 | 2/2007 |
| WO | 2007/123345 | A1 | 11/2007 |
| WO | 2007/135099 | A1 | 11/2007 |
| WO | 2007123342 | A1 | 11/2007 |
| WO | 2008/119054 | A1 | 10/2008 |
| WO | 2008/139419 | A1 | 11/2008 |
| WO | 2009/048673 | A2 | 4/2009 |
| WO | 2009/055587 | A1 | 4/2009 |
| WO | 2009072003 | A2 | 6/2009 |
| WO | 2009/122216 | A1 | 10/2009 |
| WO | 2011/019874 | A1 | 2/2011 |
| WO | 2011/133630 | A1 | 10/2011 |
| WO | 2011/133632 | A1 | 10/2011 |
| WO | 2011/133759 | A1 | 10/2011 |
| WO | 2011/133760 | A1 | 10/2011 |

OTHER PUBLICATIONS

Halbach, Design of Permanent Multipole Magnets with Oriented Rare Earth Cobalt Material, Nuclear Instrum Methods, 169:1-10 (1980).
Harada, et al., Monoclonal antibody G6K12 specific for membrane-associated differentiation marker of human stratified squamous epithelia and squamous cell carcinoma, J. Oral. Pathol. Med., 22(4):1145-152 (1993).
Harkins and Harrigan, "Labeling of Bacterial Pathogens for Flow Cytometric Detection and Enumeration" Curr Prot Cytom (2004) 11.17.1-11.17.20.
Harlow, et al., 1988, 'Antibodies', Cold Spring Harbor Laboratory, pp. 93-117.
Harris et al., Science 320:106-109 (2008).
Heijnen et al., 2009, Method for rapid detection of viable *Escherichia coli* in water using real-time NASBA, Water Research, 43:3124-3132.
Hijmans, et al., An immunofluorescence procedure for the detection of intracellular immunoglobulins, Clin. Exp. Immunol., 4:457 (1969).
Hinnisdales et al., Biotechniques Res., 19:4193 (1996).
Hirsch, et al., Easily reversible desthiobiotin binding to streptavidin, avidin, and other biotin-binding proteins: uses for protein labeling, detection, and isolation, Anal. Biochem., 208(2):343-57 (2002).
Hoult and Richards, The Signal-to-Noise Ratio of the Nuclear Magnetic Resonance Experiment, J. Magn. Reson., 24:71-85 (1976).
Hunter, et al., Immunoassays for Clinical Chemistry, pp. 147-162, Churchill Livingston, Edinborough (1983).
Inai, et al., Immunohistochemical detection of an enamel protein-related epitope in rat bone at an early stage of osteogenesis, Histochemistry, 99(5):335-362 (1993).
International Search Report for PCT/US2013/076649 with an International filing date of Dec. 19, 2013, 2 pages.
International Search Report in PCT/US2011/33184, dated Jul. 25, 2011, 2 pages.
International Search Report in PCT/US2011/33186, dated Jun. 22, 2011, 1 page.
International Search Report in PCT/US2011/33410, dated Jul. 19, 2011, 2 pages.
International Search Report in PCT/US2011/33411, dated Jun. 22, 2011, 1 page.
International Search Report issued in PCT/US2013/076649, dated Feb. 27, 2014.
ISR and Written Opinion in PCT/US2008/058518, date of issuance Sep. 29, 2009, 15 pages.
ISR and Written Opinion in PCT/US2008/058518, dated Jul. 7, 2008, 21 pages.
ISR and Written Opinion in PCT/US2008/062473, dated Oct. 29, 2008, 20 pages.
ISR and Written Opinion in PCT/US2008/080983, dated Mar. 3, 2009, 14 pages.
ISR and Written Opinion in PCT/US2009/067577, dated Feb. 5, 2010, 13 pages.
ISR and Written Opinion in PCT/US2011/48447, dated Dec. 22, 2011, 7 pages.
ISR and Written Opinion in PCT/US2011/48452, dated Dec. 22, 2011, 7 pages.
Johne, et al., *Staphylococcus aureus* exopolysaccharide in vivo demonstrated by immunomagnetic separation and alectron microscopy, J. Clin. Microbiol. 27:1631-1635 (1989).
Johnson, Thermal Agitation of Electricity in Conductors, Phys. Rev., 32:97-109 (1928).
Kaittanis, et al., One-step nanoparticle mediated bacterial detection with magentic relaxation, Nano Lett., 7(2):381-383 (2007).
Klaschik, S., L. E. Lehmann, et al. (2002). "Real-time PCR for detection and differentiation of gram-positive and gram-negative bacteria." J Clin Microbiol 40(11): 4304-4307.
Kleinstruer, "Microfluidics and Nanofluidics: Theory and Selected Applications," John Wiley & Sons, 2013.
Lecomte et al. Nucl Acids Res. 11:7505 (1983).
Lee, et al., Chip-NRM Biosensor for detection and molecular analysis of cells, Nature Medicine, 14(8):869-874 (2008).
Levin, Cell 88:5-8 (1997).
Li et al., 2010, Chemiluminescent Detect of *E. coli* O157:H7 Using Immunological Method Based on Magnetic Nanoparticles, J. of Nanoscience and Nanotechnology 10:696-701.
Life Technologies, "Dynabeads® for Immunoassay IVD", retrieved from http://www.invitrogen.com/site/us/en/home/Productsand-Services/Applications/Diagnostics-Clinical-Research/Bead-based-IVD-Assays/Bead-based-Immunoassay-IVD.html on May 29, 2013, four pages.
Lu et al., 2007, Magnetic Nanoparticles: Synthesis, Protection, Functionalization, and Application, Angew. Chem. Int. Ed. 46:1222-1244.
Lund, et al. Immunomagnetic separation and DNA hybridization for detection of enterotoxigenic *Escherichia coli* in a piglet model, J. Clin. Microbiol., 29:2259-2262 (1991).
Madonna A J, et al. "Detection of Bacteria from Biological Mixtures Using Immunomagnetic Separation Combined with Matrix-Assisted Laser Desorption/Ionization Time-of-flight Mass Spectrometry", Rapid Communications in Mass Spectrometry, John Wiley & Sons, GB, vol. 15, No. 13, Jan. 1, 2001, pp. 1068-1074.
Magin, et al., Miniature Magnetic Resonance Machines, IEEE Spectrum 34(10):51-61 (1997).
Malba, et al., Laser-lathe Lithography—A Novel Method for Manufacturing Nuclear Magnetic Resonance Microcoils, Biomed. Microdev., 5:21-27 (2003).
Maniatis et al., Molecular Cloning: A Laboratory Manual, 1982, Cold Spring Harbor, NY, pp. 280-281.
Margin, et al., High resolution microcoil 1H-NMR for mass-limited, nanoliter-vol. samples, Science, 270:1967 (1995).
Margulies et al., Nature, 437: 376-380 (2005).
Massin, et al., Planar Microcoil-based magnetic resonance imaging of cells, Transducers '03, The 12th Int. Conf. on Solid State Sensors, Actuators, and Microsystems, Boston, Jun. 8-12, pp. 967-970 (2003).
Massin, et al., Planar Microcoil-based Microfluidic NMR Probes, J. Magn. Reson., 164:242-255 (2003).
Williams and Wang, Microfabrication of an electromagnetic power micro-relay using SU-8 based UV-LIGA technology, Microsystem Technologies, 10(10):699-705 (2004).
Wu, et al., 1H-NMR Spectroscopy on the Nanoliter Scale for Static and On-Line Measurements, Anal. Chem., 66:3849 (1994).
Yang et al., "Simultaneous Detection of *Escherichia coli* O157:H7 and *Salmonella typhimurium* Using Quantum Dots as Fluorescence Labels", Analyst 131(3), Mar. 2006, pp. 394-101 (8 Pages).
Yeung et al., 2002, Quantitative Screening of Yeast Surface-Displayed Polypeptide Libraries by Magnetic Bead Capture. Biotechnol. 18:212-220.
Yu et al. "Development of a Magnetic Microplate Chemifluorimmunoassay for Rapid Detection of Bacteria and Toxin in Blood", Analytical Biochemistry 261 (1998), pp. 1-7.

(56) References Cited

OTHER PUBLICATIONS

Zhao, et al., A rapid bioassay for single bacterial cell quantitation using bioconjugated nanoparticles, PNAS, 101(42):15027-15032 (2004).
Zordan, et al., Detection of Pathogenic *E coli* O157:H7 by a Hybrid Microfluidic SPR and Molecular Imaging Cytometry Device, Cytometry A, 75A:155-162 (2009).
Matar et al., 1990, Magnetic particles derived from iron nitride, IEEE Transactions on magnetics 26(1):60-62.
McDowell, et al., Low-Field Micro-Coil Probe Development for Portable NMR, 8th ICMRM, The Heidelberg Conference, Mibu, Japan, Aug. 22-26, 2005, Conference Program Abstract, 1 page.
McDowell, et al., Operating Nanoliter Scale NMR Microcoils in a Itesla Field, J. Mag. Reson., 188(1):74-82 (2007).
Minard, et al., Solenoidal Microcoil Design, Part I: Optimizing RF Homogeneity and coil dimensions, Concepts in Magn. Reson., 13(2):128-142 (2001).
Moreira et al., 2008, Detection of *Salmonella typhimurium* in Raw Meats using In-House Prepared Monoclonal Antibody Coated Magnetic Beads and PCR Assay of the fimA Gene. Journal of Immunoassay & Immunochemistry 29:58-69.
Moresi and Magin, Miniature Permanent Magnet for Table-top NMR, Concept. Magn. Res., 19B:35-43 (2003).
Moudrianakis et al., Proc. Natl. Acad. Sci. 53:564-71 (1965).
Mulder, et al., Characterization of two human monoclonal antibodies reactive with HLA-B12 and HLA-B60, respectively, raised by in vitro secondary immunization of peripheral blood lymphocytes, Hum. Immunol., 36(3):186-192 (1993).
Myers and Gelfand, Biochemistry 30:7661 (1991).
Narang et al., Methods Enzymol., 68:90 (1979).
Nordstrom et al., J. Biol. Chem. 256:3112 (1981).
Nyquist, Thermal Agitation of Electrical Charge in Conductors, Phys. Rev., 32:110-113 (1928).
Ohno et al, 2011, Effects of Blood Group Antigen-Binding Adhesin Expression during Helicobacter pylori Infection of Mongolian Gerbils, The Journal of Infectious Diseases 203:726-735.
Olson, et al., High-resolution microcoil NMR for analysis of mass-limited, nanoliter samples, Anal. Chem., 70:645-650 (1998).
Olsvik_et_al_Magnetic_Seperation_Techniques_in_Diagnostic_Microbiology_Clinical_Microbiol_Rev_1994_7_43_54.
Pappas, et al., Cellular Separations: A Review of New Challenges in Analytical Chemistry, Analytica Chimica Acta, 601(1):26-35 (2007).
Payne, M.J. et al., "The Use of Immobilized Lectins in the Separation of *Staphylococcus aureus, Escherichia coli, Listeria* and *Salmonella* spp. from Pure Cultures and Foods", Journal of Applied Bacteriology, 1992, No. 73, pp. 41-52 (12 Pages).
Peck, et al., Design and Analysis of Microcoils for NMR Microscopy, J. Magn. Reson. B 108:114-124 (1995).
Peck, et al., RF Microcoils patterned using microlithographic techniques for use as microsensors in NMR, Proc. 15th Ann. Int. Conf. of the IEEE, Oct. 28-31, pp. 174-175 (1993).
Perez, et al., Viral-induced self-assembly of magnetic nanoparticle allows detection of viral particles in biological media, J. Am. Chem. Soc., 125:10192-10193 (2003).
Qiu, et al., Immunomagnetic separation and rapid detection of bacteria using bioluminescence and microfluidics, Talanta, 79:787-795 (2009).
Rogers, et al., Using microcontact printing to fabricate microcoils on capillaries for high resolution proton nuclear magnetic resonance on nanoliter volumes, Appl. Phys. Lett., 70:2464-2466 (1997).
Safarik et al., "The application of magnetic separations in applied Microbiology" Journal of Applied Bacteriology 1995, 78, 575-585.
Sambrook and Russell, Molecular Cloning: A Laboratory Manual 3Ed, Cold Spring Harbor Laboratory Press, 2001.
Seeber, et al., Design and Testing of high sensitivity Microreceiver Coil Apparatus for Nuclear Magnetic Resonance and Imaging, Rev. Sci. Inst., 72:2171-2179 (2001).
Seeber, et al., Triaxial Magnetic Field Gradient System for Microcoil Magnetic Resonance Imaging, Rev. Sci. Inst., 71:4263-4272 (2000).
Sillerud, et al., 1H NMR Detection of Superparamagnetic Nanoparticles at 1 T using a Microcoil and Novel Tuning Circuit, J. Magn. Reson. 181:181-190 (2006).
Sista et al., 2008, Heterogeneous Immunoassays Using Magnetic beads on a Digital Microfluidic Platform, Lab Chip 8(2):2188-2196.
Skjerve, et al., Detection of Listeria monocytogenes in foods by immunomagnetic separation, Appl. Env. Microbiol., 56:3478 (1990).
Soni et al., Clin Chem 53:1996-2001 (2007).
Sorli, et al., Micro-spectrometer for NMR: analysis of small quantities in vitro, Meas. Sci. Technol., 15:877-880 (2004).
Stanley, Essentials in Immunology and Serology, Delmar, pp. 153-153 (2002).
Stauber, et al. Rapid generation of monoclonal antibody-secreting hybridomas against African horse sickness virus by in vitro immunization and the fusion/cloning technique, J. Immunol. Methods, 161(2): 157-168 (1993).
Stenish and McGowan, Biochim Biophys Acta, 475:32 (1977).
Stocker, et al., Nanoliter volume, high-resolution NMR Microspectroscopy using a 60 um planer microcoil, IEEE Trans. Biomed. Eng., 44:1122-1127 (1997).
Subramanian, et al., RF Microcoil Design for Practical NMR of Mass-Limited Samples, J. Magn. Reson., 133:227-231 (1998).
Takagi et al., Appl. Environ. Microbiol. 63:4504 (1997).
Taktak, et al., Multiparameter Magnetic Relaxation Switch Assays, Analytical Chemistry, 79(23):8863-8869 (2007).
The United States Naval Research Laboratory (NRL), "The FABS Device: Magnetic Particles", retrieved from http://www.nrl.navy.mil/chemistry/6170/6177/beads.php on Jan. 8, 2013, two pages.
Torensama, et al., Monoclonal Antibodies Specific for the Phase-Variant O-Acetylated Ki Capsule of *Escerichia coli*, J. Clin. Microbiol., 29(7):1356-1358 (1991).
Trumbull, et al., Integrating microfabricated fluidic systems and NMR spectroscopy, IEEE Trans. Biomed. Eng., 47(1):3-7 (2000).
Van Bentum, et al., Towards Nuclear Magnetic Resonance (MU)-Spectroscopy and (MU)-Imaging, Analyst, Royal Society of Chemistry, London, 129(9):793-803 (2004).
Vandeventer, J. Clin. Microbiol. Jul. 2011, 49(7):2533-39.
Venkateswaran, et al., Production of Anti-Fibroblast Growth Factor Receptor Monoclonal Antibodies by In Vitro Immunization, Hybridoma, 11(6):729-739 (1992).
Verma, Biochim Biophys Acta. 473:1-38 (1977).
Vermunt, et al., Isolation of salmonelas by immunomagnetic separation, J. Appl. Bact., 72:112-118 (1992).
Wang and Irudayaraj, Multifunctional Magnetic-Optical Nanoparticle Probes for Simultaneous Detection, Separation, and Thermal Ablation of Multiple Pathogens, Small, 6(2):283-289 (2010).
Wang Hong, Ph.D., "Rapid and Simultaneous Detection of Foodborne Bacterial Pathogens Using Multiplex Assays", Dissertation Abstract, University of Arkansas, 2010 (2 Pages).
Webb and Grant, Signal-to-Noise and Magnetic Susceptibility Tradeoffs in Solenoidal Microcoils for NMR, J. Magn. Reson. B, 113:83-87 (1996).
Wensink, et al., High Signal to Noise Ratio in Low-field NMR on a Chip: Simulations and Experimental Results, 17th IEEE MEMS, 407-410 (2004).
Abagram, Principles of Nuclear Magnetism, Carendon Press, Oxford, 1961, pp. 71-83.
Agrawal et al., 1990, Tetrahedron Letters 31:1543-46.
Andreassen, Jack, "One micron magnetic beads optimised for automated immunoassays" as Published in CLI Apr. 2005, retrieved from http://www.cli-online.com/uploads/tx_ttproducts/datasheet/one-micron-magnetic-beads-optimised-for-automatedimmunoassays.pdf on Dec. 28, 2015, four pages.
Armenean, et al., NMR Radiofrequency Microcoil Design: Electromagnetic Simulation Usefulness, Compes Rendus Biologies, 325(4):457-463 (2002).
Armenean, et al., Solenoidal and Planar Microcoils for NMR Spectroscopy, Proc. of the 25th Annual Int. Conf. of the IEEE Eng. in Med. and Bio. Soc., Cancun, Mexico, Sep. 17, 2003, pp. 3045-3048.
Barany et al., Gene, 108:1 (1991).
Barany F. (1991) PNAS 88:189-193.
Barany, F., Genome research, 1:5-16 (1991).

(56) References Cited

OTHER PUBLICATIONS

Behnia and Webb, Limited-Sample NNR Using Solenoidal Microcoils, Perfluorocarbon Plugs, and Capillary Spinning, Anal. Chem., 70:5326-5331 (1998).
Braslaysky et al., PNAS, 100:3690-3694 (2003).
Brown et al., Methods Enzymol., 68:109 (1979).
Bruno et al., "Development of an Immunomagnetic Assay System for Rapid Detection of Bacteria and Leukocytes in Body Fluids," J Mol Recog, 9 (1996) 474-479.
Burtis et al. (Burtis, C.A. (Ed.), Tietz Textbook of Clinical Chemistry, 3rd Edition (1999), W.B. Saunders Company, Philadelphia, PA, pp. 1793-1794).
Butter et al., 2002, Synthesis and properties of iron ferrofluids, J. Magn. Magn. Mater. 252:1-3.
Byrne, et al., Antibody-Based Sensors: Principles, Problems and Potential for Detection of Pathogens and Associated Toxins, Sensors, 9:4407-4445 (2009).
Campuzano, et al., Bacterial Isolation by Lectin Modified Microengines, Nano Lett. Jan. 11, 2012; 12(1): 396-401.
Cann et al., Proc. Natl. Acad. Sci. 95:14250 (1998).
Cariello et al., Nucl Acids Res, 19:4193 (1991).
Carroll, N. M., E. E. Jaeger, et al. (2000). "Detection of and discrimination between grampositive and gram-negative bacteria in intraocular samples by using nested PCR." J Clin 15 Microbiol 38(5): 1753-1757.
Chandler et al., Automated immunomagnetic separation and microarray detection of *E. Coli* O157:H7 from poultry carcass rinse, Int. J. Food Micro., 70 (2001) 143-154.
Chapman, et al., Use of commercial enzyme immunoassays and immunomagnetic separation systems for detecting *Escherichia coli* O157 in bovine fecal samples, Applied and Environmental Microbiology, 63(7):2549-2553 (1997).
Cheng et al, 2012, Concentration and detection of bacteria in virtual environmental samples based on non-immunomagnetic separation and quantum dots by using a laboratory-made system, Proc. of SPIE:82310Y-1-82310Y-18.
Chien et al., J. Bacteriol, 127:1550 (1976).
Chungang Wang et al. "Multifunctional Magnetic-OPtical Nanoparticle Probes for Simultaneous Detection, Separation, and Thermal Ablation of Multiple Pathogens", Small, vol. 6, No. 2 Jan. 18, 2010, pp. 283-289.
Ciobanu and Pennington, 3D Micron-scale MRI of Single Biological Cells, Solid State Nucl. Magn. Reson., 25:138-141 (2004).
Cold Spring Harbor Protocols, Recipe for Dulbecco's phosphate-buffered saline (Dulbecco's PBS, 2009, retrieved from http://cshprotocols.cshlp.Org/content/2009/3/pdb.rec11725. full?text_only=true on Mar. 9, 2015, one page.
Cooper et al., 2011, A micromagnetic flux concentrator device for isolation and visualization of pathogens. 15th International Conference on Miniaturized Systems for Chemistry and Life Sciences. Oct. 2-6, 2011, Seattle, Washington, USA.
Cross, et al., Choice of Bacteria in Animal Models of Sepsis, Infec. Immun. 61(7):2741-2747 (1983).
Dam et al. "Garlic (*Allium sativum*) Lectins Bind to High Mannose Oligosaccharide Chains", Journal of Biological Chemistry vol. 273, No. 10, Issue of Mar. 6, pp. 5528-5535, 1998.
Diaz et al., Braz J. Med. Res., 31:1239 (1998).
Djukovic, et al., Signal Enhancement in HPLC/Microcoil NMR Using Automated Column Trapping, Anal. Chem., 78:7154-7160 (2006).
DNA Replication 2nd edition, Komberg and Baker, W.H. Freeman, New York, NY (1991).
Dover, Jason E., et al. "Recent advances in peptide probe-based biosensors for detection of infectious agents." Journal of microbiological methods 78.1 (2009): 10-19.
Drancourt, et al., Diagnosis of Mediterranean Spotted Fever by Indirect Immunofluorescence of Rickettsia conorii in Circulating Endothelial Cells Isolated with Monoclonal Antibody-Coated Immunomagnetic Beads, J. Infectious Diseases, 166(3):660-663, 1992.
Dynabeads® for Immunoassay IVD, retrieved from http://www.invitrogen.com/site/i3s/en/home/Products-and-Services/Applications/DiagnosticsClinical-Research/Bead-based-IVD-Assavs/Bead-based-Immunoassav-iVD.html on May 29, 2013, four pages).
Elnifro, Elfath M., et al. "Multiplex PCR: optimization and application in diagnostic virology." Clinical Microbiology Reviews 13.4 (2000): 559-570.
Engvall, Enzyme immunoassay ELISA and EMIT, Meth. in Enzymol., 70:419-439 (1980).
Extended European Search Report issued in EP 11864030.9, dated Aug. 20, 2014.
Extended European Search Report dated Feb. 2, 2017 for European Application No. 16190239.0 (8 Pages).
Extended European Search Report, dated Oct. 15, 2013 for EP application No. 11772606.7.
Fan, et al., Self-assembly of ordered, robust, three-dimensional gold nanocrystal/silica arrays, Science, 304:567 (2004).
Fenwick et al., 1986, Mechanisms Involved in Protection Provided by Immunization against Core Lipopolysaccarides of *Escherichia coli* J5 from Lethal Haemophilus pleuropneumoniae Infections in Swine, Infection and Immunity 53(2):298-304.
Fu, et al., Rapid Detection of *Escherichia coli* O157:H7 by Immunogmagnetic Separation and Real-time PCR, Int. J. Food Microbiology, 99(1):47-57, (2005).
Fukushima et al., Experimental Pulse NMR: A Nuts and Bolts Approach, Addison-Wesley, Reading, Mass., 1981.
Fung, M-C., et al. PCR amplification of mRNA directly from a crude cell lysate prepared by thermophilic protease digestion, Nucleic Acids Research, vol. 19 (15), p. 4300, 1991.
Furdui , Vasile I. et al., "Immunomagnetic T Cell Capture From Blood for PCR Analysis Using Microfluidic Systems", Lab on a Chip, 2004, vol. 4. No. 6, pp. 614-618 (5 Pages).
Furdui , Vasile I. et al., "Microfabricated Electrolysis Pump System for Isolating Rare Cells in Blood; Micro-Electrolysis Jumps for Blood", Journal of Micromechanics & Microengineering, vol. 13, No. 4, Jul. 1, 2003, pp. S164-S170 (7 Pages).
Goding, J.W., Conjugation of antibodies with fluorochromes: modifications to the standard methods, J. Immunol. Meth. 13:215 (1976).
Goloshevsky, et al., Development of Low Field Nuclear Magnetic Resonance Microcoils, Rev. Sci. Inst.., 76:024101-1 to 024101-6 (2005).
Goloshevsky, et al., Integration of Biaxial Planar Gradient Coils and an RF Microcoil for NMR Flow Imaging, Meas. Sci. Technol., 16:505-512 (2005).

* cited by examiner

TARGET DETECTION

RELATED APPLICATION

The present application is a divisional of U.S. patent application Ser. No. 14/104,164, filed Dec. 12, 2013, which claims the benefit of and priority to U.S. provisional application Ser. No. 61/739,577, filed Dec. 19, 2012, the contents of each of which are incorporated by reference herein in their entirety.

TECHNICAL FIELD

The invention relates to methods for indicating whether an assay properly isolated or separated a target, such as a pathogen, from a sample.

BACKGROUND

Blood-borne pathogens are a significant healthcare problem. A delayed or improper diagnosis of a bacterial infection can result in sepsis, a serious, and often deadly, inflammatory response to the infection. Sepsis is a leading cause of death in the United States. Early detection of bacterial infections in blood is the key to preventing the onset of sepsis. Traditional methods of detection and identification of blood-borne infection include blood culture and antibiotic susceptibility assays. Those methods typically require culturing cells, which can be expensive and can take as long as 72 hours. Often, septic shock will occur before cell culture results can be obtained.

Pathogens during active blood-borne infection or after antibiotic treatment are typically present in minute levels per mL of body fluid. Several techniques have been developed for isolation of pathogens in a body fluid sample, which include molecular detection methods, antigen detection methods, and metabolite detection methods. These conventional methods often require culturing specimens, such as performing an incubation or enrichment step, in order to detect the low levels of pathogens. The incubation/enrichment period is intended to allow for the growth of bacteria and an increase in bacterial cell numbers to more readily aid in isolation and identification. In many cases, a series of two or three separate incubations is needed to isolate the target bacteria. Moreover, enrichment steps require a significant amount of time (e.g., at least a few days to a week) and can potentially compromise test sensitivity by killing some of the cells sought to be measured.

To avoid incubation/enrichment periods and to reduce overall time, other techniques have been developed to rapidly isolate low levels of pathogens from body fluids. Those techniques often utilize antibody bound particles specific to a target pathogen and a sorting apparatus such as an affinity column or magnetic surface. Although successful at rapidly separating small amounts of pathogens from the bodily fluid, these techniques have multiple steps, such as binding targets to the particles, binding to target/particle complexes to a sorting apparatus, isolating bound target/particle complexes from the body fluid sample, in which a failure at any step can result in the inability to isolate pathogens that are present in the bodily fluid. That is, failure at any one step can result in a failed assay.

Currently, there is no effective way to distinguish between a successful assay that correctly identifies the absence of a pathogen and a failed assay in which a pathogen was present but just not isolated. Because the failure to detect and treat blood-borne pathogens can result in significant health problems, there is a need to develop a method for rapid isolation of pathogens from a sample, such as a blood sample, that indicates whether the assay properly isolated suspected pathogens.

SUMMARY

The invention generally relates to increasing the sensitivity of assays used to isolate pathogens at very low levels within a sample. Due to technological advances, it is now possible to isolate a single bacterium from a blood sample. For example, co-pending and co-assigned U.S. application Ser. No. 13/091,534 allows for detection of pathogens in a heterogeneous biological sample at levels from about 10 CFU/mL to about 1 CFL/mL. Methods of the invention account for the fact that, when isolating pathogens at such low pathogen levels, the difference between a failed assay (i.e. failure to identify a molecule present in the sample) and a positive assay (i.e. positively determining the presence of a molecule present) is often dependent upon the capture of a single target, e.g., pathogen species, meaning, that if a particular species is not captured, the assay reports a negative result. Methods of the invention provide for differentiating between negative and positive assays to increase the accuracy of target pathogen detection.

Methods of the invention involve obtaining a sample suspected of containing a target, e.g., pathogen. To decrease the reporting of a false negative result, a detectable marker is also added to the sample. An assay is conducted to detect the suspected pathogen using magnetic particles. The detectable marker's purpose is to be sufficiently similar to the pathogen such that the assay performs functionally in the same manner for the detectable marker and the pathogen. However, during the analysis of the captured complexes, the detectable marker can be distinguished from the pathogen. Therefore, this provides a quality assurance check on the assay to ensure that the assay is functioning properly or that the magnetic particles are correctly matched with the pathogen to be detected.

In certain embodiments, at least two sets of magnetic particles are employed. In those embodiments, members of a first set of magnetic particles are coupled to a binding entity specific to the target, e.g., a pathogen, and members of a second set of magnetic particles are conjugated to a binding entity specific to the detectable marker. Alternatively, magnetic particles including more than one binding moiety (e.g, a binding moiety that is specific to the target and a binding moiety that is specific to the detectable marker) can be introduced into the sample to bind the target and the detectable marker. At the analysis step of the assay, once the presence or absence of the target is determined, the presence or absence of the detectable marker is also determined, either concurrently or subsequent to detection of the target. In some embodiments, analysis allows for the simultaneous detection of the detectable marker and the pathogen. Based on the presence or absence of the detectable marker, a determination is made about whether the assay properly functioned. Detection of the detectable marker indicates a properly executed assay.

The presence of the marker indicates that the assay worked properly; and thus any detection of pathogen (or the absence of pathogen) is accurate and not the result of a failed assay. If analysis of the isolated portion of the sample contains the detectable marker, it can be concluded that the assay properly functioned and the assay was successfully performed. However, if the isolated portion of the sample lacks the presence of the detectable marker, then the assay did not function properly and the results should not be relied upon. In a particular instance, a detectable marker can be introduced into the sample to bind with a plurality of magnetic particles to determine whether the magnetic particles employed in the assay bind properly.

Any assay for separating targets from a sample is useful according to methods of invention, including assays that utilize affinity columns and magnetic fields to isolate pathogens. In one embodiment, the assay includes introducing into a biological sample a cocktail including a plurality of sets of magnetic particles, wherein members of at least one set comprise a binding agent specific for a pathogen and members of at least one set comprise a binding agent specific to the a detectable marker. In another embodiment, magnetic particles including two or more binding moieties, are used. In such embodiments, a first binding moiety on the particle is specific to the target, e.g., pathogen, and a second binding moiety on the particle is specific to the detectable marker. In either embodiment, any pathogen present in the sample and the detectable marker bind to their respective moieties, either on the same particle or on different particles. The sample is exposed to a magnetic field to isolate bound particles (i.e., those that bind pathogen or the marker) from other components of the sample. Once isolated, the presence of the detectable marker is determined. The presence of the marker indicates that the assay worked. Thus, if no pathogen is detected, it is not the result of a failure of the assay to work, thereby eliminating a false negative result.

Any convenient method is useful for detecting the detectable marker and pathogen, including PCR, microarray hybridization, and sequencing. In certain aspects, the presence or absence of the detectable marker is determined prior to determining the presence or absence of the suspected pathogen target. Detecting the detectable marker prior to detecting any isolated pathogen reduces the time and costs associated with detecting targets in a failed assay.

Samples suitable for use in methods of the invention include, but are not limited to, biological samples, such as tissue or body fluid. Targets within the sample include eukaryotic cells, prokaryotic cells, plant cells, animal cells, fungi, bacteria, and viruses. In certain aspects, the target is a pathogen. In addition, methods of the invention also contemplate nucleic acids, proteins, receptors, ligands, or any other known molecule as a target.

In certain aspects, the detectable marker is a microbe, including a viable or nonviable microbe. The detectable marker can be sufficiently similar to the target such that the assay performs functionally in the same manner for the detectable marker and the target. The detectable marker may be labeled or otherwise modified to allow for their differentiation from targets originally present in the sample. For example, but not by way of limitation, the detectable marker can be genetically modified so as to express a fluorescent protein, or alternatively, the detectable marker could be pre-stained with a persistent stain to allow their differentiation from microbes that are originally present in the fluid composition. In addition, the detectable marker may be chosen based on a chromogen dye specific reaction to the presence of the detectable marker.

Binding entities attached to magnetic particles can be selected at the convenience of the user. In a preferred embodiment, antibodies conjugated to the magnetic particles are used and may be either monoclonal or polyclonal antibodies. Since each set of particles is conjugated with antibodies having different specificities for different pathogens and detectable markers. Compositions of the invention may be provided such that each set of antibody conjugated to a particle is present at a concentration designed for detection of a specific pathogen and specific detectable marker in the sample. In certain embodiments, all of the sets are provided at the same concentration. Alternatively, the sets are provided at different concentrations.

To facilitate detection of the different sets of pathogen/magnetic particle complexes and the detectable marker/magnetic particle complexes, the particles may be differently labeled. Any detectable label may be used with compositions of the invention, such as fluorescent labels, radiolabels, enzymatic labels, and others. In particular embodiments, the detectable label is an optically-detectable label, such as a fluorescent label. Exemplary fluorescent labels include Cy3, Cy5, Atto, cyanine, rhodamine, fluorescein, coumarin, BODIPY, alexa, and conjugated multi-dyes. In one aspect, both the detectable marker and the magnetic particle can be labeled to facilitate detection of the detectable marker.

Any type of magnetic material is suitable for use in methods of the invention. Magnetic particles generally fall into two broad categories. The first category includes particles that are permanently magnetizable, or ferromagnetic; and the second category includes particles that demonstrate bulk magnetic behavior only when subjected to a magnetic field. The latter are referred to as magnetically responsive particles. Materials displaying magnetically responsive behavior are sometimes described as superparamagnetic. However, materials exhibiting bulk ferromagnetic properties, e.g., magnetic iron oxide, may be characterized as superparamagnetic when provided in crystals of about 30 nm or less in diameter. Larger crystals of ferromagnetic materials, by contrast, retain permanent magnet characteristics after exposure to a magnetic field and tend to aggregate thereafter due to strong particle-particle interaction. In certain embodiments, the particles are superparamagnetic particles. In other embodiments, the magnetic particles include at least 70% superparamagnetic particles by weight. In certain embodiments, the superparamagnetic particles are from about 100 nm to about 250 nm in diameter. In certain embodiments, the magnetic particle is an iron-containing magnetic particle. In other embodiments, the magnetic particle includes iron oxide or iron platinum.

DETAILED DESCRIPTION

The invention generally relates to using detectable markers to indicate whether an assay is properly functioning, for example, properly separating suspected targets from a sample. Accordingly, methods of the invention provide for differentiating between negative and positive assays to increase the reliability of target pathogen detection, i.e. providing an indication that the assay positively identified the presence or absence of a target analyte in a sample. Methods of the invention involve obtaining a sample suspect of containing targets, introducing a detectable marker into the sample, and conducting an assay using a plurality of magnetic particles to isolate targets and one or more detectable markers from the sample. The plurality of magnetic particles, can include different sets whereby at least one set of the magnetic particles is coupled to binding moieties (e.g., antibodies) specific to the suspected targets and at least one set of the magnetic particles is coupled to binding moieties (e.g., antibodies) specific to the detectable marker. In other embodiments, a plurality of magnetic particles include more than one binding moiety, (e.g., antibody) specific to the target and a binding moiety (e.g., antibody) specific to the detectable marker. After conducting the assay, methods of the invention provide for making a determination about the presence or absence of the targets in the sample based on the determination of the presence or absence of the detectable marker.

Presence of the detectable marker indicates that the magnetic particles are functioning properly and that all steps of the assay were performed accurately. A lack of the detectable marker indicates either malfunction of the magnetic particles, the employment of a non-binding magnetic particle, or error in execution of the assay. Because the detectable marker was placed into the sample, the subsequent determination of the presence or absence of the detectable marker indicates whether the assay properly bound the detectable marker to the magnetic particle or if the assay failed because it was unable to bind the detectable marker.

Methods of the invention involve collecting a sample, such as a tissue or body fluid. The sample may be collected in any clinically acceptable manner. A body fluid having a target can be collected in a container, such as a blood collection tube (e.g., VACUTAINER (test tube specifically designed for venipuncture, commercially available from Becton, Dickinson and company). In certain embodiments, a solution is added that prevents or reduces aggregation of endogenous aggregating factors, such as heparin in the case of blood.

A body fluid refers to a liquid material derived from, for example, a human or other mammal. Such body fluids include, but are not limited to, mucus, blood, plasma, serum, serum derivatives, bile, phlegm, saliva, sweat, amniotic fluid, mammary fluid, urine, sputum, and cerebrospinal fluid (CSF), such as lumbar or ventricular CSF. A body fluid may also be a fine needle aspirate. A body fluid also may be media containing cells or biological material. In particular embodiments, the fluid is blood.

A tissue is a mass of connected cells and/or extracellular matrix material, e.g. skin tissue, nasal passage tissue, CNS tissue, neural tissue, eye tissue, liver tissue, kidney tissue, placental tissue, mammary gland tissue, placental tissue, gastrointestinal tissue, musculoskeletal tissue, genitourinary tissue, bone marrow, and the like, derived from, for example, a human or other mammal and includes the connecting material and the liquid material in association with the cells and/or tissues. A sample may also be a fine needle aspirate or biopsied tissue. A sample also may be media containing cells or biological material.

Although directed towards the isolation and detection of pathogens, methods of the invention may be used to isolate and detect any target. The target analyte refers to the substance suspected to be present in the sample that will be captured and isolated by methods of the invention. The target may be bacteria, fungi, a protein, a cell (such as a cancer cell, a white blood cell a virally infected cell, or a fetal cell circulating in maternal circulation), a virus, a nucleic acid (e.g., DNA or RNA), a receptor, a ligand, a hormone, a drug, a chemical substance, or any molecule known in the art. In certain embodiments, the suspected target is a pathogenic bacterium, fungus, or virus. In other embodiments, the target is a gram positive or gram negative bacteria. Exemplary bacterial species that may be captured and isolated by methods of the invention include *E. coli, Listeria, Clostridium, Mycobacterium, Shigella, Borrelia, Campylobacter, Bacillus, Salmonella, Staphylococcus, Enterococcus, Pneumococcus, Streptococcus*, and a combination thereof.

Aspects of the invention involve introducing one or more detectable markers into the sample suspected of containing a target or pathogen. Any object capable of isolation and detection from a sample using an assay can be used as the detectable marker. In one embodiment, the detectable marker that has similar properties to the suspected pathogen or targets that one desires to isolate or capture. This ensures that the assay is essentially functioning the same for both the suspected targets and the detectable marker. Any concentration of detectable markers can be introduced into the sample. For example, the concentration of detectable markers introduced is the same as an estimated amount of targets or pathogens suspected of being present in the sample. In another example, 1 to 10 detectable markers are introduced per mL of sample fluid.

Suitable detectable markers for use in the invention include a bacteria, fungi, a protein, a cell (such as a cancer cell, a white blood cell a virally infected cell, or a fetal cell circulating in maternal circulation), a virus, a nucleic acid (e.g., DNA or RNA), a receptor, a ligand, a hormone, a drug, a chemical substance, or any molecule known in the art. Preferably, the detectable marker does not have cross reactivity with the suspected target. In certain aspects, the detectable marker is a microbe, or microorganism. In one embodiment, the microbe is a non-viable microbe or viable mircrobe.

The detectable marker may be labeled or otherwise modified to allow for their differentiation from targets or pathogens originally present in the sample. For example, but not by way of limitation, the detectable marker could be genetically modified so as to express a fluorescent protein, or alternatively, the detectable marker could be pre-stained with a persistent stain to allow their differentiation from microbes that are originally present in the sample fluid. In addition, the detectable marker microbe may be chosen based on a specific-reaction to a chromogen.

In one aspect, the detectable marker is pre-stained using the FISH method, which is a method of fluorescence-staining a microbe by using a nucleic acid probe and targeting a nucleic acid in a cell. This method does not require the step of extracting a nucleic acid from a microbe, and directly adds a fluorescence-labeled nucleic acid probe to a pretreated microbe to make the probe hybridize to an rRNA or chromosome DNA of a nucleic acid in a microbial cell. In general, an rRNA of a nucleic acid in a microbial cell is used as a probe target. There are several thousand to several hundred thousand rRNA copies in a microbial cell, and hence there are probe targets equal in number to the rRNA copies. For this reason, a large amount of fluorescent dye bonded to the nucleic acid probe is accumulated in the target microbial cell. When the fluorescent dye used in this case is irradiated with proper excitation light, only the target microbial cell emits fluorescence without changing its shape to allow its observation under the epifluorescent microscope.

In another aspect, the detectable marker may be genetically modified or engineered to include a protein or other marker capable of being visualized. For example, the detectable marker can be modified with the GFP (Green Fluorescent Protein) gene or Luciferase reported gene. In this manner, the DTMO may be visualized non-invasively using appropriate UV or other suitable illumination and imaging conditions.

Alternatively, in another embodiment, the detectable marker is not pre-labeled or dyed prior to being introduced into the sample, but rather the detectable marker is labeled or differentiated from the target after the assay for detection. For example, the detectable marker can be contacted with antibodies specific to the detectable marker, and the antibody is labeled either directly or indirectly with labels used in known immunoassays.

In another example, the detectable marker is chosen based on a chromogen's reaction to the detectable marker, i.e. the chromogen undergoes a change in color based on the presence of the microbe. Any of a variety of different types of microbes may generally be detected by microbe-sensitive chomogen such as bacteria, fungi, viruses, mold, yeast, etc, and can detect microbes of various different shapes, cell arrangements, and compositions. Microbe-sensitive chromogens suitable for use in methods of the invention include, for example, any chromogen that undergoes a readily detectable change in color based on the chromogen's interaction with microbe.

Microbe specific chromogens suitable for use in the invention include a light absorbing chromophore that is a light-absorbing portion of the chromogen responsible for the chromogen's change of color. Common chromophores include azo groups (e.g., azo dyes), polyene groups (e.g., carotene dye), and carbonyl groups (e.g., anthraquinone dyes), and the chromophores may be connected to a conjugated system. Solvatochromic dyes are a class of chromogen that can be used to detect microbes. U.S. Pat. No. 7,300,770 details various types and characteristics of microbe sensitive chromogens.

Suitable solvatochromic dyes may include, but are not limited to merocyanine dyes (e.g., mono-, di-, and tri-merocyanines), betaine dyes, such as 4-2,4,6-triphenylpyridinium-1-yl)-2,6-diphenylphenolate (Reichardt's dye), 4-dicyanmethylene-2-methyl-6-(p-dimethylaminostyryl)-4H-pyran (DCM); 6-propionyl-2-(dimethylamino)naphthalene (PRODAN); 9-(diethylamino)-5H-benzo[a]phenox-azin-5-one (Nile Red); 4-(dicyanovinyl)julolidine (DCVJ); phenol blue; stilbazolium dyes; coumarin dyes; ketocyanine dyes; N,N-dimethyl-4-nitroaniline (NDMNA) and N-methyl-2-nitroaniline (NM2NA); Nile blue; 1-anilinonaphthalene-8-sulfonic acid (1,8-ANS), and dapoxylbutylsulfonamide (DBS) and other dapoxyl analogs.

Still other suitable dyes that may be used in the present invention include, but are not limited to, 4-[2-N-substituted-1,4-hydropyridin-4-ylidine)ethylidene]cyclohexa-2,5-di-en-1-one, red pyrazolone dyes, azomethine dyes, indoaniline dyes, and mixtures thereof. and merocyanine dyes (e.g., mono-, di-, and tri-merocyanines) are one example of a type of solvatochromic dye.

Methods of the invention provide for conducting an assay to isolate any suspected targets or pathogens and the detectable markers from the sample. To ensure the assay is properly working, the steps for isolating the target or pathogens and the detectable markers should be the same. Assays suitable for use in methods of the invention include, for example, affinity chromatography assays and immunomagnetic assays. Affinity chromatography assays utilizes differences in cell surface macromolecules by passing sample fluids containing the cells through what is known as an affinity column, wherein the affinity column is typically a porous membrane containing binding moieties specific to the target. Examples of affinity chromatography column assays for separating pathogens from sample include those described in Ashok Kumar, Akshay Srivastava. Cell separation using cryogel-based affinity chromatography, Nature protocols 2010; 5:1737-1747; Brewster J. D., Isolation and concentration of *Salmonellae* with an immunoaffinity column, J Microbiol Methods. 2003 Oct; 55(1):287-93; Wang et al. Open-Tubular Capillary Cell Affinity Chromatography: Single and Tandem Blood Cell Separation, Anal. Chem. 2008, 80, 2118-2124.

In one aspect, the assay includes introducing a plurality of magnetic particles to the sample. The magnetic particles are divided into at least two sets. Particles of at least one set includes a pathogen specific binding moieties and particles of at least one other set include detectable marker specific binding moieties. Other sets can be used with binding moieties specific to different targets, such as a third set specific to a second target, a fourth set specific to a third target, a fifth set specific to a fourth target, etc. The sample is allowed to incubate to allow the magnetic particles to bind to the pathogens and the detectable markers. After incubation, the sample is subject to a magnetic field to capture pathogen/magnetic particles complexes and detectable marker/magnetic particles complexes on a surface. Optionally, after the complexes are bound, the surface is washed with a wash solution that reduces particle aggregation, thereby isolating the complexes.

In another aspect of the invention, the assay includes introducing a plurality of the magnetic particles into the sample, where a particles includes more than one binding moiety. That is, a single particle includes at least two binding moieties. In such embodiments, a first binding moiety on the particle is specific for binding to the target, e.g., pathogen, and a second binding moiety is specific for binding to the detectable marker. Such particles are further described, for example in Zeng, H. and Sun, S. (2008), Syntheses, Properties, and Potential Applications of Multicomponent Magnetic Nanoparticles. Adv. Funct. Mater., 18: 391-400. doi: 10.1002/adfm.200701211; see also J. Mater. Chem., 2004, 14, 1336-1341, DOI: 10.1039/B315103D, accepted 13 Feb. 2004, the content of each of which is incorporated by reference herein in its entirety.

In certain embodiments, the detectable marker and the pathogen have similar binding moieties such that a single binding moiety can bind to either the pathogen or the detectable marker.

In other embodiments, a magnetic particle may have two or more antibodies specific to different pathogens. In other embodiments, a magnetic particle may be conjugated to an antibody specific to a pathogen and a lectin specific to a different pathogen.

Composition used in methods of the invention may use any type of magnetic particle. Production of magnetic particles and particles for use with the invention are known in the art. See for example Giaever (U.S. Pat. No. 3,970,518), Senyi et al. (U.S. Pat. No. 4,230,685), Dodin et al. (U.S. Pat. No. 4,677,055), Whitehead et al. (U.S. Pat. No. 4,695,393), Benjamin et al. (U.S. Pat. No. 5,695,946), Giaever (U.S. Pat. No. 4,018,886), Rembaum (U.S. Pat. No. 4,267,234), Molday (U.S. Pat. No. 4,452,773), Whitehead et al. (U.S. Pat. No. 4,554,088), Forrest (U.S. Pat. No. 4,659,678), Liberti et al. (U.S. Pat. No. 5,186,827), Own et al. (U.S. Pat. No. 4,795,698), and Liberti et al. (WO 91/02811), the content of each of which is incorporated by reference herein in its entirety.

Magnetic particles generally fall into two broad categories. The first category includes particles that are permanently magnetizable, or ferromagnetic; and the second category includes particles that demonstrate bulk magnetic behavior only when subjected to a magnetic field. The latter are referred to as magnetically responsive particles. Materials displaying magnetically responsive behavior are sometimes described as superparamagnetic. However, materials exhibiting bulk ferromagnetic properties, e.g., magnetic iron oxide, may be characterized as superparamagnetic when provided in crystals of about 30 nm or less in diameter. Larger crystals of ferromagnetic materials, by contrast, retain permanent magnet characteristics after exposure to a magnetic field and tend to aggregate thereafter due to strong particle-particle interaction. In certain embodiments, the particles are superparamagnetic particles. In certain embodiments, the magnetic particle is an iron containing magnetic particle. In other embodiments, the magnetic particle includes iron oxide or iron platinum.

In certain embodiments, the magnetic particles include at least about 10% superparamagnetic particles by weight, at least about 20% superparamagnetic particles by weight, at least about 30% superparamagnetic particles by weight, at least about 40% superparamagnetic particles by weight, at least about 50% superparamagnetic particles by weight, at least about 60% superparamagnetic particles by weight, at least about 70% superparamagnetic particles by weight, at least about 80% superparamagnetic particles by weight, at least about 90% superparamagnetic particles by weight, at least about 95% superparamagnetic particles by weight, or at least about 99% superparamagnetic particles by weight. In a particular embodiment, the magnetic particles include at least about 70% superparamagnetic particles by weight.

In certain embodiments, the superparamagnetic particles are less than 100 nm in diameter. In other embodiments, the superparamagnetic particles are about 150 nm in diameter, are about 200 nm in diameter, are about 250 nm in diameter, are about 300 nm in diameter, are about 350 nm in diameter, are about 400 nm in diameter, are about 500 nm in diameter, or are about 1000 nm in diameter. In a particular embodiment, the superparamagnetic particles are from about 100 nm to about 250 nm in diameter.

In certain embodiments, the particles (e.g., nanoparticles) incorporate magnetic materials, or magnetic materials that have been functionalized, or other configurations as are known in the art. In certain embodiments, nanoparticles may be used that include a polymer material that incorporates magnetic material(s), such as nanometal material(s). When those nanometal material(s) or crystal(s), such as $Fe_3O_4$, are superparamagnetic, they may provide advantageous properties, such as being capable of being magnetized by an external magnetic field, and demagnetized when the external magnetic field has been removed. This may be advantageous for facilitating sample transport into and away from an area where the sample is being processed without undue particle aggregation.

One or more or many different nanometal(s) may be employed, such as $Fe_3O_4$, FePt, or Fe, in a core-shell configuration to provide stability, and/or various others as may be known in the art. In many applications, it may be advantageous to have a nanometal having as high a saturated moment per volume as possible, as this may maximize gradient related forces, and/or may enhance a signal associated with the presence of the particles. It may also be advantageous to have the volumetric loading in a particle be as high as possible, for the same or similar reason(s). In order to maximize the moment provided by a magnetizable nanometal, a certain saturation field may be provided. For example, for $Fe_3O_4$ superparamagnetic particles, this field may be on the order of about 0.3 T.

The size of the nanometal containing particle may be optimized for a particular application, for example, maximizing moment loaded upon a target, maximizing the number of particles on a target with an acceptable detectability, maximizing desired force-induced motion, and/or maximizing the difference in attached moment between the labeled target and non-specifically bound targets or particle aggregates or individual particles. While maximizing is referenced by example above, other optimizations or alterations are contemplated, such as minimizing or otherwise desirably affecting conditions.

In an exemplary embodiment, a polymer particle containing 80 wt % $Fe_3O_4$ superparamagnetic particles, or for example, 90 wt % or higher superparamagnetic particles, is produced by encapsulating superparamagnetic particles with a polymer coating to produce a particle having a diameter of about 250 nm.

In certain embodiments, the plurality of magnetic particles are divided into two or more sets, in which a first set of the particles has a target-specific binding moiety that allows for binding the target of interest in the sample, and a second set of the particles has a binding moiety that specifically binds of the detectable marker. In other embodiments, a plurality of magnetic particles include more than one binding moiety, e.g., a binding moiety (e.g., antibody) specific to the target and a binding moiety (e.g., antibody) specific to the detectable marker.

The target-specific moiety may be any molecule known in the art and will depend on the target to be captured and isolated. Exemplary target-specific binding moieties include nucleic acids, proteins, ligands, antibodies, aptamers, and receptors.

In particular embodiments, the target-specific binding moiety is an antibody, such as an antibody that binds a particular bacterium. General methodologies for antibody production, including criteria to be considered when choosing an animal for the production of antisera, are described in Harlow et al. (Antibodies, Cold Spring Harbor Laboratory, pp. 93-117, 1988). For example, an animal of suitable size such as goats, dogs, sheep, mice, or camels are immunized by administration of an amount of immunogen, such the target bacteria, effective to produce an immune response. An exemplary protocol is as follows. The animal is injected with 100 milligrams of antigen resuspended in adjuvant, for example Freund's complete adjuvant, dependent on the size of the animal, followed three weeks later with a subcutaneous injection of 100 micrograms to 100 milligrams of immunogen with adjuvant dependent on the size of the animal, for example Freund's incomplete adjuvant. Additional subcutaneous or intraperitoneal injections every two weeks with adjuvant, for example Freund's incomplete adjuvant, are administered until a suitable titer of antibody in the animal's blood is achieved. Exemplary titers include a titer of at least about 1:5000 or a titer of 1:100,000 or more, i.e., the dilution having a detectable activity. The antibodies are purified, for example, by affinity purification on columns containing protein G resin or target-specific affinity resin.

The technique of in vitro immunization of human lymphocytes is used to generate monoclonal antibodies. Techniques for in vitro immunization of human lymphocytes are well known to those skilled in the art. See, e.g., Inai, et al., Histochemistry, 99(5):335 362, May 1993; Mulder, et al., Hum. Immunol., 36(3):186 192, 1993; Harada, et al., J. Oral Pathol. Med., 22(4):145 152, 1993; Stauber, et al., J. Immunol. Methods, 161(2):157 168, 1993; and Venkateswaran, et al., Hybridoma, 11(6) 729 739, 1992. These techniques can be used to produce antigen-reactive monoclonal antibodies, including antigen-specific IgG, and IgM monoclonal antibodies.

Any antibody or fragment thereof having affinity and specific for the bacteria of interest is within the scope of the invention provided herein. Immunomagnetic particles against *Salmonella* are provided in Vermunt et al. (J. Appl. Bact. 72:112, 1992). Immunomagnetic particles against *Staphylococcus aureus* are provided in Johne et al. (J. Clin. Microbiol. 27:1631, 1989). Immunomagnetic particles against Listeria are provided in Skjerve et al. (Appl. Env.

Microbiol. 56:3478, 1990). Immunomagnetic particles against *Escherichia coli* are provided in Lund et al. (J. Clin. Microbiol. 29:2259, 1991).

Methods for attaching the target-specific binding moiety to the magnetic particle are known in the art. Coating magnetic particles with antibodies is well known in the art; see for example Harlow et al. (Antibodies, Cold Spring Harbor Laboratory, 1988), Hunter et al. (Immunoassays for Clinical Chemistry, pp. 147-162, eds., Churchill Livingston, Edinborough, 1983), and Stanley (Essentials in Immunology and Serology, Delmar, pp. 152-153, 2002). Such methodology can easily be modified by one of skill in the art to bind other types of target-specific binding moieties to the magnetic particles. Certain types of magnetic particles coated with a functional moiety are commercially available from Sigma-Aldrich (St. Louis, Mo.).

Since each set of particles is conjugated with antibodies having different specificities for the suspected target or detectable marker, compositions used in methods of the invention may be provided such that each set of antibody conjugated particles is present at a concentration designed for detection of one or more different suspected targets and one or more detectable markers in the sample. In certain embodiments, sets for the suspected targets and detectable markers are provided at the same concentration. Alternatively, the sets are provided at different concentrations if, for example, there are more than one suspected targets in the sample. For example, compositions may be designed such that sets that bind gram positive bacteria are added to the sample at a concentration of $2\times10^9$ particles per/mL, while sets that bind gram negative bacteria are added to the sample at a concentration of $4\times10^9$ particles per/mL. Compositions used with methods of the invention are not affected by antibody cross-reactivity. However, in certain embodiments, sets are specifically designed such that there is no cross-reactivity between different antibodies and different sets.

Capture of a wide range of suspected pathogens or targets and the detectable marker simultaneously can be achieved by utilizing antibodies specific to target. Further, expanded reactivity can be achieved by mixing particles of different reactivity. The addition of high concentrations of non-specific particles does not interfere with the capture efficiency of target-specific particles.

In certain aspects, methods of the invention provide for differentially labeling the magnetic particles specific to the targets and the detectable marker for subsequent detection. Although the detectable marker can be detected on its own, the particle specific to the detectable marker is also labeled so that the detectable marker is subject to the same assay as the suspected pathogens. This is because aspects of the invention provide for conducting the same assay on the detectable markers as the suspected pathogens to ensure the assay functions essentially the same for both the detectable marker and the suspected pathogens. In this embodiment, the detectable marker can be detected on its own or through use of the detectable label attached to the magnetic particle.

To facilitate detection of the pathogen/magnetic particle complexes the particles may be differently labeled. Any detectable label may be used with compositions of the invention, such as fluorescent labels, radiolabels, enzymatic labels, and others. The detectable label may be directly or indirectly detectable. In certain embodiments, the exact label may be selected based, at least in part, on the particular type of detection method used. Exemplary detection methods include radioactive detection, optical absorbance detection, e.g., UV-visible absorbance detection, optical emission detection, e.g., fluorescence; phosphorescence or chemiluminescence; Raman scattering. Preferred labels include optically-detectable labels, such as fluorescent labels. Examples of fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'tetramethyl-6-carboxyrhodamine (TAMRA); tetramethyl rhodamine; tetramethyl rhodamine isothiocyanate (TRITC); riboflavin; rosolic acid; terbium chelate derivatives; Atto dyes, Cy3; Cy5; Cy5.5; Cy7; IRD 700; IRD 800; La Jolta Blue; phthalo cyanine; and naphthalo cyanine. Preferred fluorescent labels are cyanine-3 and cyanine-5. Labels other than fluorescent labels are contemplated by the invention, including other optically-detectable labels. Methods of linking fluorescent labels to magnetic particles or antibodies are known in the art.

The sample suspected of containing pathogens/targets and one or more detectable markers is then mixed with compositions as described above to generate a mixture that is allowed to incubate such that the plurality of magnetic particles bind to one or more suspected pathogens, if any, and one or more detectable markers in the sample. The mixture is allowed to incubate for a sufficient time to allow for the composition to bind to the pathogens and detectable markers. The process of binding the composition to the pathogen associates a magnetic moment with the pathogen, and thus allows the pathogen to be manipulated through forces generated by magnetic fields upon the attached magnetic moment.

In general, incubation time will depend on the desired degree of binding between the pathogen, detectable markers and the magnetic particles of the invention (e.g., the amount of moment that would be desirably attached to the pathogen), the amount of moment per target, the amount of time of mixing, the type of mixing, the reagents present to promote the binding and the binding chemistry system that is being employed. Incubation time can be anywhere from about 5 seconds to a few days. Exemplary incubation times range from about 10 seconds to about 2 hours. Binding occurs over a wide range of temperatures, generally between 15° C. and 40° C.

In certain embodiments, a buffer solution is added to the sample along with the compositions of the invention. An exemplary buffer includes Tris(hydroximethyl)-aminomethane hydrochloride at a concentration of about 75 mM. It has been found that the buffer composition, mixing parameters (speed, type of mixing, such as rotation, shaking etc., and temperature) influence binding. If labeled, it is important to maintain osmolality of the final solution (e.g., blood+buffer) to maintain high label efficiency. In certain embodiments, buffers used in methods of the invention are designed to prevent lysis of blood cells or any other cells, facilitate efficient binding of targets with magnetic particles and to reduce formation of particle aggregates. It has been found that the buffer solution containing 300 mM NaCl, 75 mM Tris-HCl pH 8.0 and 0.1% Tween 20 meets these design goals.

Without being limited by any particular theory or mechanism of action, it is believed that sodium chloride is mainly responsible for maintaining osmolality of the solution and for the reduction of non-specific binding of magnetic particle through ionic interaction. Tris(hydroximethyl)-aminomethane hydrochloride is a well-established buffer compound frequently used in biology to maintain pH of a solution. It has been found that 75 mM concentration is beneficial and sufficient for high binding efficiency. Likewise, Tween 20 is widely used as a mild detergent to decrease nonspecific attachment due to hydrophobic interactions. Various assays use Tween 20 at concentrations ranging from 0.01% to 1%. The 0.1% concentration appears to be optimal for the efficient labeling of bacteria, while maintaining blood cells intact.

Additional compounds can be used to modulate the capture efficiency by blocking or reducing non-specific interaction with blood components and either magnetic particles or pathogens. For example, chelating compounds, such as EDTA or EGTA, can be used to prevent or minimize interactions that are sensitive to the presence of $Ca^{2+}$ or $Mg^{2+}$ ions.

An alternative approach to achieve high binding efficiency while reducing time required for the binding step is to use static mixer, or other mixing devices that provide efficient mixing of viscous samples at high flow rates, such as at or around 5 mL/min. In one embodiment, the sample is mixed with binding buffer in ratio of, or about, 1:1, using a mixing interface connector. The diluted sample then flows through a mixing interface connector where it is mixed with target-specific nanoparticles. Additional mixing interface connectors providing mixing of sample and antigen-specific nanoparticles can be attached downstream to improve binding efficiency. The combined flow rate of the labeled sample is selected such that it is compatible with downstream processing.

After binding of the particles to the pathogen and detectable markers in the sample to form pathogen/magnetic particle complexes, a magnetic field is applied to the mixture to capture the complexes on a surface. Components of the mixture that are not bound to magnetic particles will not be affected by the magnetic field and will remain free in the mixture. Methods and apparatuses suitable for separating target/magnetic particle complexes and detectable marker/magnetic particles from other components of a mixture are known in the art. For example, a steel mesh may be coupled to a magnet, a linear channel or channels may be configured with adjacent magnets, or quadrapole magnets with annular flow may be used. Other methods and apparatuses for separating target/magnetic particle complexes from other components of a mixture are shown in Rao et al. (U.S. Pat. No. 6,551,843), Liberti et al. (U.S. Pat. No. 5,622,831), Hatch et al. (U.S. Pat. No. 6,514,415), Benjamin et al. (U.S. Pat. No. 5,695,946), Liberti et al. (U.S. Pat. No. 5,186,827), Wang et al. (U.S. Pat. No. 5,541,072), Liberti et al. (U.S. Pat. No. 5,466,574), and Terstappen et al. (U.S. Pat. No. 6,623,983), the content of each of which is incorporated by reference herein in its entirety.

In certain embodiments, the magnetic capture is achieved at high efficiency by utilizing a flow-through capture cell with a number of strong rare earth bar magnets placed perpendicular to the flow of the sample. When using a flow chamber with flow path cross-section 0.5 mm×20 mm (h×w) and 7 bar NdFeB magnets, the flow rate could be as high as 5 mL/min or more, while achieving capture efficiency close to 100%. In one embodiment, alternating magnetic fields are applied to the complexes to encourage binding of the complexes to the surface. Additionally, binding moieties specific to the target/magnetic particle complex and detectable marker/magnetic particle complex can be used to further enhance binding of complexes to the surface. Methods of capture using alternating magnetic fields and surface binding moieties are described in co-pending and co-owned U.S. patent application Ser. No. 12/855,147 (U.S. Patent Publication No. 2011-0262893).

The above described type of magnetic separation produces efficient capture of one or more targets and one more detectable markers and the removal of a majority of the remaining components of a sample mixture. However, such a process produces a sample that contains a very high percent of magnetic particles that are not bound to targets or detectable markers because the magnetic particles are typically added in excess, as well as non-specific target entities. Non-specific target entities may for example be bound at a much lower efficiency, for example 1% of the surface area, while a target of interest might be loaded at 50% or nearly 100% of the available surface area or available antigenic cites. However, even 1% loading may be sufficient to impart force necessary for trapping in a magnetic gradient flow cell or sample chamber.

For example, in the case of immunomagnetic binding of bacteria or fungi in a blood sample, the sample may include: bound targets and detectable markers at a concentration of about 1/mL or a concentration less than about $10^6$/mL; background particles at a concentration of about $10^7$/mL to about $10^{10}$/mL; and non-specific targets at a concentration of about 10/mL to about $10^5$/mL.

The presence of magnetic particles that are not bound to targets or detectable marker and non-specific target entities on the surface along with the target/magnetic particle complexes detectable marker/magnetic particle complexes interferes with the ability to successfully detect or isolate the target of interest. The magnetic capture of the resulting mix, and close contact of magnetic particles with each other and bound targets, result in the formation of aggregate that is hard to dispense and which might be resistant or inadequate for subsequent processing or analysis steps. In order to remove magnetic particles that are not bound to target analytes and non-specific target entities, the surface may be washed with a wash solution that reduces particle aggregation, thereby isolating target/magnetic particle complexes from the magnetic particles that are not bound to target analytes and non-specific target entities. The wash solution minimizes the formation of the aggregates.

Any wash solution that imparts a net negative charge to the magnetic particle that is not sufficient to disrupt interaction between the target-specific moiety of the magnetic particle and the target analyte may be used. Without being limited by any particular theory or mechanism of action, it is believed that attachment of the negatively charged molecules in the wash solution to magnetic particles provides net negative charge to the particles and facilitates dispersal of non-specifically aggregated particles. At the same time, the net negative charge is not sufficient to disrupt strong interaction between the target-specific moiety of the magnetic particle and the target analyte (e.g., an antibody-antigen interaction). Exemplary solutions include heparin, Tris-HCl, Tris-borate-EDTA (TBE), Tris-acetate-EDTA (TAE), Tris-cacodylate, HEPES (4-(2-hydroxyethyl)-1-piperazineethanesulphonic acid), PBS (phosphate buffered saline), PIPES (piperazine-N,N'-bis(2-ethanesulfonic acid), MES (2-N-morpholino)ethanesulfonic acid), Tricine (N-(Tri (hydroximethyl)methyl)glycine), and similar buffering agents. In certain embodiments, only a single wash cycle is performed. In other embodiments, more than one wash cycle is performed.

In particular embodiments, the wash solution includes heparin. For embodiments in which the body fluid sample is blood, the heparin also reduces probability of clotting of blood components after magnetic capture. The bound targets and detectable markers are washed with heparin-containing buffer 1-3 times to remove blood components and to reduce formation of aggregates.

Once the assay is complete and the target/magnetic particle complexes and detectable marker complexes are isolated from the sample, methods of the invention provide for detecting the presence of the detectable marker in order to indicate whether the assay is properly working. Detection of the detectable marker can be performed before, simultaneously, or subsequent the detection of the suspected targets. If the detectable marker is positively detected, the assay is working properly and the detection of suspected targets is positively confirmed. In other words, detection of the detectable marker indicates proper functionality of the magnetic particle and proper execution of the assay. If the detectable marker is not detected, then the assay or the magnetic particles failed in capturing the target and detectable marker. These results should not be relied upon, and can prompt quality assurance investigations and remedies. In certain aspects, the detectable marker is detected prior to detection of the targets. This allows one to confirm that the assay is working prior to expending resources for detecting targets in what may result in a failed assay. In certain aspects, the detectable marker and the target are detected simultaneously, negating the need for two analysis steps.

The detectable marker and target may be analyzed by a multitude of existing technologies, such as miniature NMR, Polymerase Chain Reaction (PCR), mass spectrometry, fluorescent labeling and visualization using microscopic observation, fluorescent in situ hybridization (FISH), growth-based antibiotic sensitivity tests, and variety of other methods that may be conducted with purified target without significant contamination from other sample components.

In one embodiment, the detectable marker is detected using the microbe sensitive chromogens discussed in detail above. After the assay, the remaining contents, i.e. magnetically captured detectable markers and targets, are placed in a final collection tube. To determine if the assay worked properly, a chromogen specific to the detectable marker is placed in the tube in such an amount to undergo a detectable color change in the presence of the detectable marker. If the color appears, this color change indicates that the detectable marker has been properly captured, indicating that the assay and magnetic particles functioned properly. Then the contents can be analyzed for the presence or absence of targets in the sample. In another embodiment, chromogens specific to the target are used to detect the presence or absence of the target.

In another embodiment, isolated target and/or detectable marker are lysed with a chaotropic solution, and DNA is bound to DNA extraction resin. After washing of the resin, the DNA is eluted and used in quantitative RT-PCR to detect the presence of the target and/or detectable marker.

In certain embodiments, magnetic particles are introduced into the sample, where the magnetic particles contain at least one set to bind to the binding specific moiety of the target and at least one set to bind to the binding specific moiety of the detectable target. A magnetic field is applied to the sample, thereby capturing the magnetic particles onto a surface. After the assay, the presence of the detectable marker is determined for proper functioning of the assay.

In other embodiments, magnetic particles are introduced into the sample, where the magnetic particles are capable of binding to the target and to the detectable marker. Meaning, that each magnetic particle contains at least two different sites, wherein one site the target is bound and in a second site the detectable marker is bound. For example, each particle contains at least two types of binding moieties on each particle for binding the target and the detectable marker. After the assay, the presence of the detectable marker is determined for proper functioning of the assay.

In another embodiment, the detectable marker and target are removed from the magnetic particles to which they are bound and the processed sample is mixed with fluorescent labeled antibodies specific to each. After incubation, the reaction mixture is filtered through 0.2 μm to 1.0 μm filter to capture labeled detectable markers and targets while allowing majority of free beads and fluorescent labels to pass through the filter. The detectable markers and targets are visualized on the filter using microscopic techniques, e.g. direct microscopic observation, laser scanning or other automated methods of image capture. The presence of detectable markers and target is detected through image analysis. After the results of the assay are confirmed based on the positive presence of the detectable marker, any targets isolated from the sample can be further characterized using PCR or genomic methods.

If the targets are bacteria, detection of the bacteria can be performed by use of nucleic acid probes following procedures which are known in the art. Suitable procedures for detection of bacteria using nucleic acid probes are described, for example, in Stackebrandt et al. (U.S. Pat. No. 5,089,386), King et al. (WO 90/08841), Foster et al. (WO 92/15883), and Cossart et al. (WO 89/06699), each of which is hereby incorporated by reference.

A suitable nucleic acid probe assay generally includes sample treatment and lysis, hybridization with selected probe(s), hybrid capture, and detection. Lysis of the bacteria is necessary to release the nucleic acid for the probes. The nucleic acid target molecules are released by treatment with any of a number of lysis agents, including alkali (such as NaOH), guanidine salts (such as guanidine thiocyanate), enzymes (such as lysozyme, mutanolysin and proteinase K), and detergents. Lysis of the bacteria, therefore, releases both DNA and RNA, particularly ribosomal RNA and chromosomal DNA both of which can be utilized as the target molecules with appropriate selection of a suitable probe. Use of rRNA as the target molecule(s), may be advantageous because rRNAs constitute a significant component of cellular mass, thereby providing an abundance of target molecules. The use of rRNA probes also enhances specificity for the bacteria of interest, that is, positive detection without undesirable cross-reactivity which can lead to false positives or false detection.

Hybridization includes addition of the specific nucleic acid probes. In general, hybridization is the procedure by which two partially or completely complementary nucleic acids are combined, under defined reaction conditions, in an anti-parallel fashion to form specific and stable hydrogen bonds. The selection or stringency of the hybridization/reaction conditions is defined by the length and base composition of the probe/target duplex, as well as by the level and geometry of mis-pairing between the two nucleic acid strands. Stringency is also governed by such reaction parameters as temperature, types and concentrations of denaturing agents present and the type and concentration of ionic species present in the hybridization solution.

The hybridization phase of the nucleic acid probe assay is performed with a single selected probe or with a combination of two, three or more probes. Probes are selected having sequences which are homologous to unique nucleic acid sequences of the target organism. In general, a first capture probe is utilized to capture formed hybrid molecules. The hybrid molecule is then detected by use of antibody reaction or by use of a second detector probe which may be labelled with a radioisotope (such as phosphorus-32) or a fluorescent label (such as fluorescein) or chemiluminescent label.

Detection of bacteria of interest can also be performed by use of PCR techniques. A suitable PCR technique is described, for example, in Verhoef et al. (WO 92/08805). Such protocols may be applied directly to the bacteria captured on the magnetic beads. The bacteria are combined with a lysis buffer and collected nucleic acid target molecules are then utilized as the template for the PCR reaction.

For detection of the selected bacteria by use of antibodies, isolated bacteria are contacted with antibodies specific to the bacteria of interest. As noted above, either polyclonal or monoclonal antibodies can be utilized, but in either case have affinity for the particular bacteria to be detected. These antibodies will adhere/bind to material from the specific target bacteria. With respect to labeling of the antibodies, these are labeled either directly or indirectly with labels used in other known immunoassays. Direct labels may include fluorescent, chemiluminescent, bioluminescent, radioactive, metallic, biotin or enzymatic molecules. Methods of combining these labels to antibodies or other macromolecules are well known to those in the art. Examples include the methods of Hijmans, W. et al. (1969), Clin. Exp. Immunol. 4, 457-, for fluorescein isothiocyanate, the method of Goding, J. W. (1976), J. Immunol. Meth. 13, 215-, for tetramethylrhodamine isothiocyanate, and the method of Ingrall, E. (1980), Meth. in Enzymol. 70, 419-439 for enzymes.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for detecting a target and confirming proper functioning of an assay, the method comprising obtaining a sample suspected of containing a target;

introducing a detectable marker into the sample;

incubating the sample to allow for coupling of the detectable marker and the target, if present, to magnetic particles comprising both a first binding moiety specific to the target and a second binding moiety specific to the detectable marker in the sample;

conducting an assay using magnetic particles to isolate the detectable marker and the target from the sample;

determining the presence or absence of the target in the sample; and confirming proper function of the assay by determining presence or absence of the detectable marker.

2. The method of claim 1, wherein the detectable marker comprises a microbe.

3. The method of claim 2, wherein the microbe is detectable via a microbe-sensitive chromogen.

4. The method of claim 1, wherein the detectable marker comprises a label.

5. The method of claim 4, wherein the label is a fluorescent label.

6. The method of claim 1, wherein the target is selected from the group consisting of cells, bacteria, viruses, fungi, and any combination thereof.

7. The method of claim 1, wherein the assay comprises exposing the magnetic particles to a magnetic field.

8. The method of claim 7, wherein the assay further comprises flowing the sample through a channel comprising surface binding moieties specific to the targets and to the detectable marker attached to a surface of the channel; and binding the magnetic particles to the surface of the channel, wherein the step of applying a magnetic field brings the magnetic particles coupled to the target and detectable marker into proximity of the surface to facilitate binding of magnetic particles to the surface of the channel; and washing away unbound magnetic particles and unbound sample components.

9. The method of claim 1, wherein the method further comprises introducing the magnetic particles into the sample, wherein the magnetic particles are introduced prior to the conducting an assay step.

10. The method of claim 1, wherein the presence of the target is determined separately from the presence of the detectable marker.

* * * * *